United States Patent [19]

Psaros et al.

[11] Patent Number: 5,471,979
[45] Date of Patent: Dec. 5, 1995

[54] METHOD AND APPARATUS FOR THE REUSE OF ANESTHETIC GASES IN INHALATION ANESTHEIA WITH SPECIFIC SIZE AND POSITION OF $CO_2$ ABSORBER

[75] Inventors: George Psaros, Tullinge; Sven-Gunnar Olsson, Arloev, both of Sweden

[73] Assignee: Siemens Aktiengesellschaft, Munich, Germany

[21] Appl. No.: 263,953

[22] Filed: Jun. 22, 1994

Related U.S. Application Data

[63] Continuation of Ser. No. 695,268, May 3, 1991, abandoned.

[30] Foreign Application Priority Data

May 3, 1990 [SE] Sweden .................... 90015819

[51] Int. Cl.⁶ ............................. A62B 7/10; A62B 23/02
[52] U.S. Cl. .................... 128/205.28; 128/205.12; 128/203.12; 128/205.27
[58] Field of Search ........................ 128/203.14, 203.12, 128/203.25, 203.28, 204.13–204.18, 204.21, 204.22, 205.11–205.15, 205.17, 205.18, 205.27–205.29

[56] References Cited

U.S. PATENT DOCUMENTS

| | | |
|---|---|---|
| 3,713,440 | 1/1973 | Nicholes . |
| 4,150,670 | 4/1979 | Jewett et al. . |
| 4,360,018 | 11/1982 | Chokski . |
| 4,534,346 | 8/1985 | Schlaechter ............ 128/205.12 |
| 4,611,590 | 9/1986 | Ryschka et al. ............ 128/203.14 |
| 4,905,685 | 3/1990 | Olsson et al. ............ 128/203.12 |
| 4,989,597 | 2/1991 | Werner ............ 128/205.12 |
| 5,044,361 | 9/1991 | Werner et al. ............ 128/203.12 |
| 5,094,235 | 3/1992 | Westenskow et al. ............ 128/204.22 |
| 5,119,810 | 6/1992 | Kiske et al. ............ 128/203.12 |

FOREIGN PATENT DOCUMENTS

| | | |
|---|---|---|
| 167364 | 6/1959 | Sweden . |
| WO8807876 | 10/1988 | WIPO . |

*Primary Examiner*—Kimberly L. Asher
*Attorney, Agent, or Firm*—Hill, Steadman & Simpson

[57] ABSTRACT

A method and apparatus for the re-use of anesthetic gases which are not absorbed by a patient, in inhalation anesthesia make use of an adsorption filter during exhalation, the unused anesthetic gases being subsequently desorbed from the adsorption filter during inhalation, and being reintroduced into the respiration flow to the patient. The exhaled gas is supplied through an absorber for carbon dioxide before it is re-supplied to the patient. The apparatus includes a common line for the delivery and discharge of anesthesia and respiration gases to and from a patient. An adsorption filter for adsorption and desorption of anesthetic gases is arranged in this line. To prevent the carbon dioxide from the exhalation gas of the patient, which is adsorbed in the adsorption material, from being re-supplied to the patient in the next inhalation phase, the common line between the patient and the adsorption filter is at least partially divided into an inhalation branch and an exhalation branch, with an absorber for carbon dioxide disposed in the inhalation branch, sized to match the small amount of carbon dioxide left in the reintroduced gas.

11 Claims, 3 Drawing Sheets

METHOD AND APPARATUS FOR THE REUSE OF ANESTHETIC GASES IN INHALATION ANESTHEIA WITH SPECIFIC SIZE AND POSITION OF $CO_2$ ABSORBER

This is a continuation of application Ser. No. 07/695,268, filed May 3, 1991, now abandoned.

BACKGROUND OF THE INVENTION

1. Field of the Invention

The present invention is directed to a method and apparatus for inhalation anesthesia, and in particular to such a method and apparatus which permits re-use of anesthetic gases.

2. Description of the Prior Art

A patient respiration system is described in Swedish published application 459 155 wherein fresh respiration gas is mixed with an anesthetic from an anesthetic gasifier in a collecting line entering and departing the patient, and the exhalation gas from the patient passes through an adsorption filter. The anesthetic which is not absorbed by the patient is adsorbed by the adsorption filter, whereas the majority portion of the exhalation gas passes through the filter. During inhalation of the patient, the adsorbed anesthetic is desorbed from the adsorption material in the filter, and is re-supplied to the patient. It is unavoidable, however, that a slight amount of carbon dioxide from the exhalation gas of the patient is adsorbed in the adsorption material in the filter, and this will be subsequently desorbed and is re-supplied to the patient during the inhalation phase.

SUMMARY OF THE INVENTION

It is an object of the present invention to provide a method and apparatus for reuse of anesthetic gases in inhalation anesthesia wherein carbon dioxide, from the exhalation gas of the patient, is prevented from being re-supplied to the patient during the next inhalation phase.

The object is achieved in accordance with the principles of the present invention in a method and apparatus which employ a carbon dioxide absorber disposed so that at least the gas which has passed through the adsorption filter passes through the carbon dioxide adsorber before it is re-supplied to the patient. The gas mix will thus be free of carbon dioxide when it reaches the patient. The absorber can be made relatively small because it must only absorb a relatively small amount of carbon dioxide during the inhalation phase.

It is not practical to use a carbon dioxide absorber in the common line between the adsorption filter and the patient in the arrangement disclosed in the aforementioned Swedish published application No. 459 155, because such an absorber in that arrangement would have to be extremely large in order to absorb all of the carbon dioxide from the exhalation gas of the patient. Due to its size, the absorber would create an unacceptably high exhalation resistance.

In a further embodiment of the invention, the gas concentration, of a selected type of gas, is measured between the patient and the absorber and is used for controlling the fresh respiration or the anesthetic gas which is supplied to the gas mix. The patient thus always receives the intended gas concentration.

In a further embodiment of the method, the above control is undertaken using feedback, whereby the measured gas concentration forms the actual value and the intended gas concentration defines the desired or regulated value. Automatic regulation of the gas concentration which is supplied to the patient is achieved by means of such feedback control.

The apparatus of the invention includes a common line for the delivery and discharge of anesthetic and respiration gases to and from a patient. An adsorption filter, which contains adsorption material for the adsorption and desorption of anesthetic gas, is disposed in this line. The apparatus also includes a second line for the delivery of the anesthetic and/or respiration gases to the patient past the adsorption filter. The common line between the patient and the adsorption filter is at least partially divided into an inhalation branch and an exhalation branch. An absorber for carbon dioxide is disposed in the inhalation branch. The absorber absorbs residues of carbon dioxide, so that no carbon dioxide is re-supplied to the patient in the inhalation phase.

In a further embodiment of the apparatus, carbon is used as the adsorption material. Carbon is an extremely good adsorption material for anesthetic such as, for example, halothane. Carbon is also an extremely good moisture adsorbent, and consequently represents a good moisture-heat exchanger. Due to the high absorbability of carbon, the adsorption filter can be made relatively small.

The adsorption filter and the adsorber are attached in parallel, and at a distance from each other, in a common container or housing, so that a first channel is formed between the adsorption filter and the absorber, a second channel is formed between the adsorption filter and a first inside wall of the container, and a third channel is formed between the absorber and a second inside wall of the container. The first channel is connected to the exhalation branch, the second channel is connected to the common line at that side of the adsorption filter facing away from the patient, and that the third channel is connected to the inhalation branch. As a result, a small, simple and inexpensive part is achieved, which contains both the adsorption filter and the absorber. This part can be a disposable component.

In a further embodiment of the apparatus, a germ filter can be disposed following the adsorption filter at the side facing away from the patient. Germs are thereby filtered out of the exhalation gas, which prevents the lines and inhalation apparatus from becoming contaminated. These portions of the apparatus, therefore, need not necessarily be cleaned after use.

In another embodiment of the apparatus, a gas conduit is connected to the common line, or to the inhalation branch, between the patient and the absorber. This gas conduit conducts a portion the gas mixture which is supplied to the patient to a measuring stage, which measures the gas concentration of at least one type of gas. A sensor signal corresponding to the measured gas concentration is supplied to a control mechanism which, by feedback, controls delivery of the anesthetic or respiration gases to the gas mixture via a line so that an intended gas concentration is supplied to the patient. Automatic regulation of the desired gas concentration which is supplied to the patient is thus always present.

DESCRIPTION OF THE PREFERRED EMBODIMENTS

Figure 1:
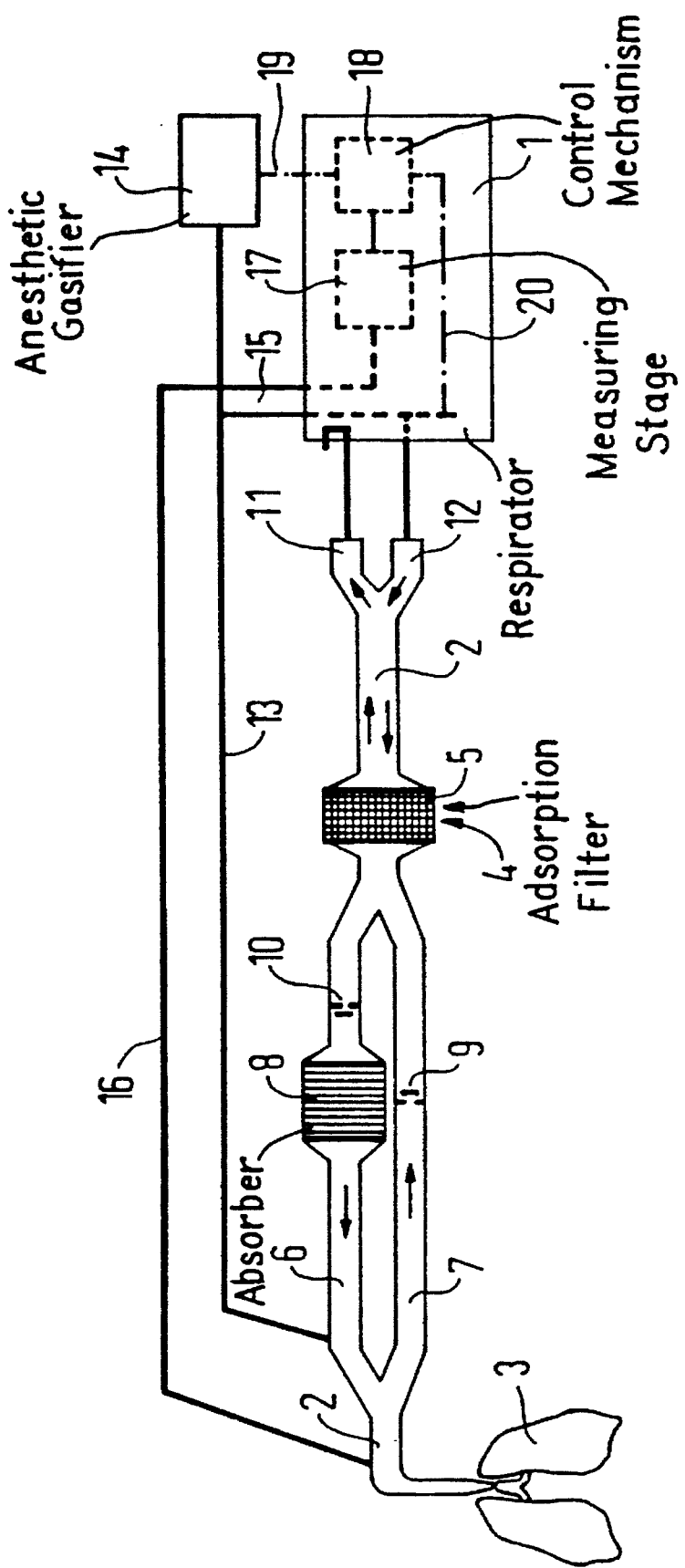
FIG. 1 is a schematic diagram of an apparatus constructed in accordance with the principles of the present invention, and operating in accordance with the principles of the method, connected to a respirator.

An apparatus for the re-use of anesthetic gases in inhalation anesthesia, constructed in accordance with the principles of the present invention and operating in accordance with the disclosed method, is shown in FIG. 1 connected to a respirator 1. The apparatus includes a common line 2 for the delivery and discharge of anesthetic and respiration gases to or from a patient 3. An adsorption filter 4, which contains an adsorption material 5 for the adsorption and desorption of anesthetic gases, is arranged in the common line 2. The line between the patient 3 and the adsorption filter 4 is partially divided into an inhalation branch 6 and an exhalation branch 7. An absorber for carbon dioxide is disposed in the inhalation branch 6. One-way valves 9 and 10 are respectively disposed in the inhalation branch 6 and the exhalation branch 7. The one-way valve 10 is disposed between the adsorption filter 4 and the absorber 8. The free end of the common line 2 forms a Y-coupling, with one branch 11 being connected via the respirator 1 to an evacuation system (not shown) for the exhalation gas, and the other branch 12 being connected to the respirator 1 for the delivery of respiration gas. A line 13 for the delivery of anesthetic gases from an anesthesia gasifier 14 is connected to the inhalation branch 6 between the absorber 8 and the patient 3. The anesthesia gasifier 14 can alternatively be disposed in the respirator 1. A line 15 is connected to the line 13, the line 15 being connected to the respirator 1 for delivering, as needed, fresh respiration gas to the patient 3 via the lines 15 and 13.

A gas conduit 16, which conducts a specimen of the gas mixture which is supplied to the patient 3 to a measuring stage 17 for measuring the gas concentration of the specimen, is connected to the line 2 between the line 13 and the patient 3. A sensor signal corresponding to the gas concentration of the gas mixture is subsequently supplied to a control mechanism 18 which, by feedback, controls delivery of anesthetic or respiration gases so that a desired gas concentration is supplied to the patient 3. The dot-dash lines 19 and 20 represent connections between the control mechanism 18 and the anesthesia gasifier 14 and between the control mechanism 18 and the line 15 and the branch 12 for discharging respiration gases. Both the measuring stage 17 and the control mechanism 18 in this exemplary embodiment are contained in the respirator 1.

In an exhalation phase, the exhaled gas from the patient 3 passes through the exhalation branch 7, the one-way valve 9 and the adsorption filter 4. The anesthetic gas, supplied in an earlier inhalation phase, which the patient 3 has not absorbed, as well as moisture from the exhalation gas and a small amount of carbon dioxide are then adsorbed in the adsorption filter 4, whereas the remainder of the exhalation gas passes through the line 2 and the branch 11 via the respirator 1, and proceeds into the evacuation system. In the inhalation phase, fresh respiration gas from the respirator 1 passes through the branch 12, the line 2 and the adsorption filter 4. The adsorbed anesthetic gas and the moisture and the adsorbed carbon dioxide are desorbed and mix with the fresh respiration gas. Because the one-way valve 9 in the exhalation branch is in a blocking state in the inhalation phase, this gas mix is conducted via the inhalation branch 6, the one-way valve 10 and the absorber 8, which absorbs the residues of the carbon dioxide in the gas mix. Before the gas mix reaches the patient 3, a specimen is taken from this mixture which, as described above, is conducted via the conduit 16 to the measuring stage 17 in the respirator 1. The measured signals are supplied to the control mechanism 18 which, dependent thereon, supplies signals to the anesthesia gasifier 14 and to the respirator 1 so that the proper quantities and the desired mixture of anesthetic and respiration gases are supplied to the patient. These gases are supplied through the line 13 to the gas mixer before they reach the patient 3. If the patient 3 is awake, the delivery of respiration gas from the respirator 1 via the common line 2 and the inhalation branch 6 is blocked. The anesthesia gasifier 14 is also shut off. As a result, the patient 3 is supplied only with fresh respiration gas from the respirator 1 via the lines 15 and 13.

Figure 2:
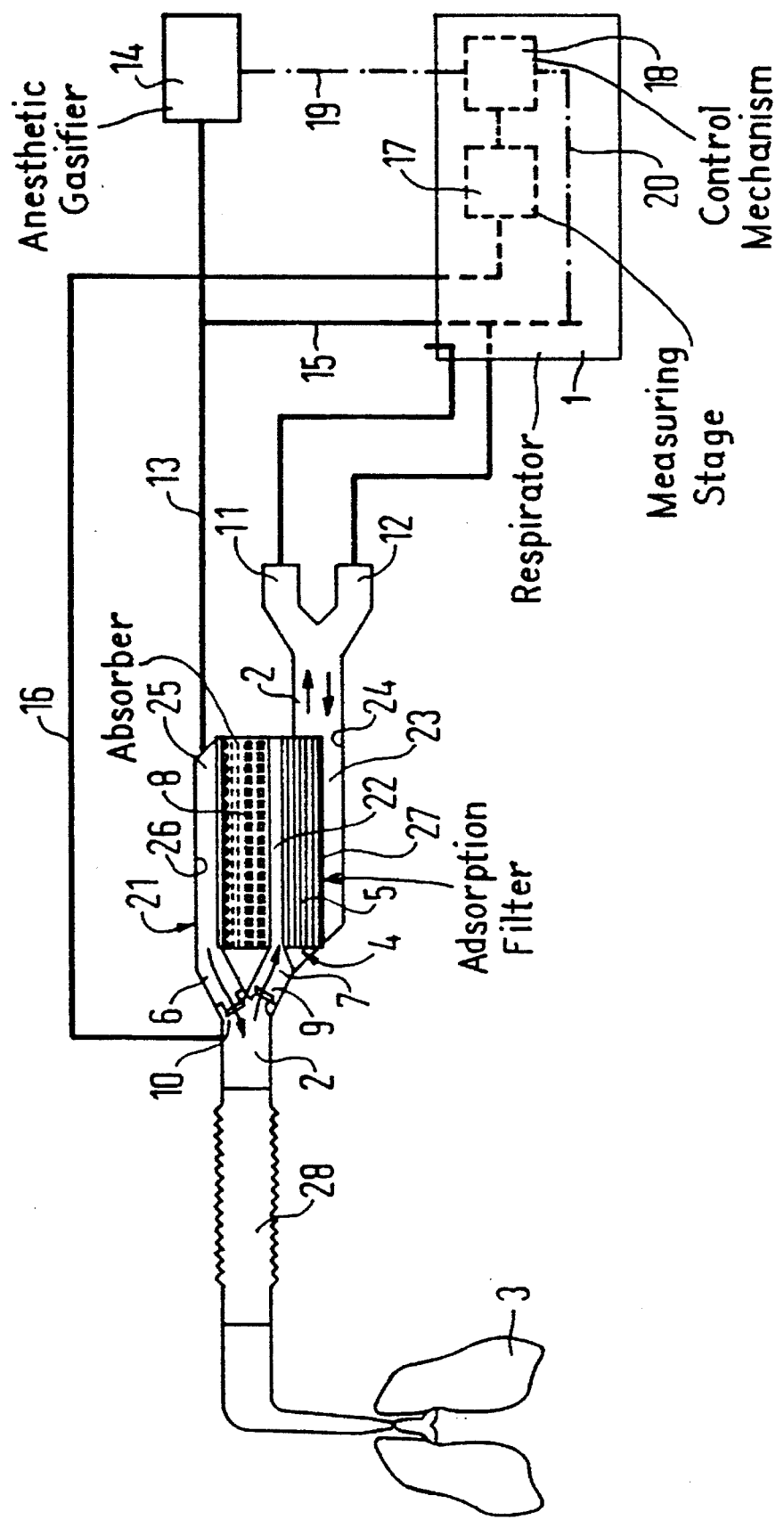
FIGS. 2 and 3 are schematic diagrams of further embodiments of the apparatus and method.

As shown in FIG. 2, the adsorption filter 4 and the absorber 8 can be connected in parallel and at a distance from each other in a container 21, in which channels are formed. A first channel 22 is formed between the adsorption filter 4 and the absorber 8. A second channel 23 is formed between the adsorption filter 4 and a first inside wall 24 of the container 21. A third channel 25 is formed between the absorber 8 and a second inside wall 26 of the container 21. One end of each of the channels 22, 23 and 25 is open, and the opposite ends of each of the channels are closed. The channel 22 is connected to the exhalation branch 7, the channel 23 is connected to the common line 2 at that side of the container 21 facing away from the patient 3, and channel 25 is connected to the inhalation branch 6.

A germ filter 27 is disposed following the adsorption filter 4 at that side thereof facing away from the patient 3. The germ filter 27 is intended to prevent germs from the exhalation gas from contaminating the hoses and the container, so that they need not necessarily be cleaned after treatment. As in the exemplary embodiments described above, an anesthesia gasifier 14 is connected via the line 13 to the closed end of the channel 25 for the delivery of fresh anesthetic gas. A measuring stage 17 is also provided which measures the gas concentration of the inhalation gas, which operates a control mechanism 18 in the manner described above to control the volume of respiration or anesthetic gases which are supplied to the patient 3.

During the exhalation phase in the embodiment of FIG. 2, the exhalation gas flows through a short, flexible hose 28, through the common line 2 and through the one-way valve 9 in the exhalation branch 7. The exhalation gas then flows through the channel 22 and subsequently passes the adsorption filter 4. Anesthetic gas and moisture from the preceding inhalation phase, which the patient 3 has not absorbed, as well as a slight quantity of carbon dioxide are adsorbed in the adsorption filter 4. The remainder of the exhalation gas is conveyed to the evacuation system through the line 2, the branch 11 and the respirator 1. In the inhalation phase, fresh respiration gas from the respirator 1 is conducted via the branch 12, the line 2, the germ filter 27 and the adsorption filter 4. The adsorbed anesthetic gas and the moisture, as well as the adsorbed carbon dioxide, are desorbed and, together with the respiration gas, are caused to pass the channel 22 and subsequently the absorber 8, wherein the carbon dioxide residues are absorbed. The gas then subsequently flows through the channel 25, the one-way valve 10, the line 2 and the hose 28 to the patient 3. As a result of the structure of this embodiment, the lines can be short, thus diminishing the unavoidable "dead space".

Figure 3:
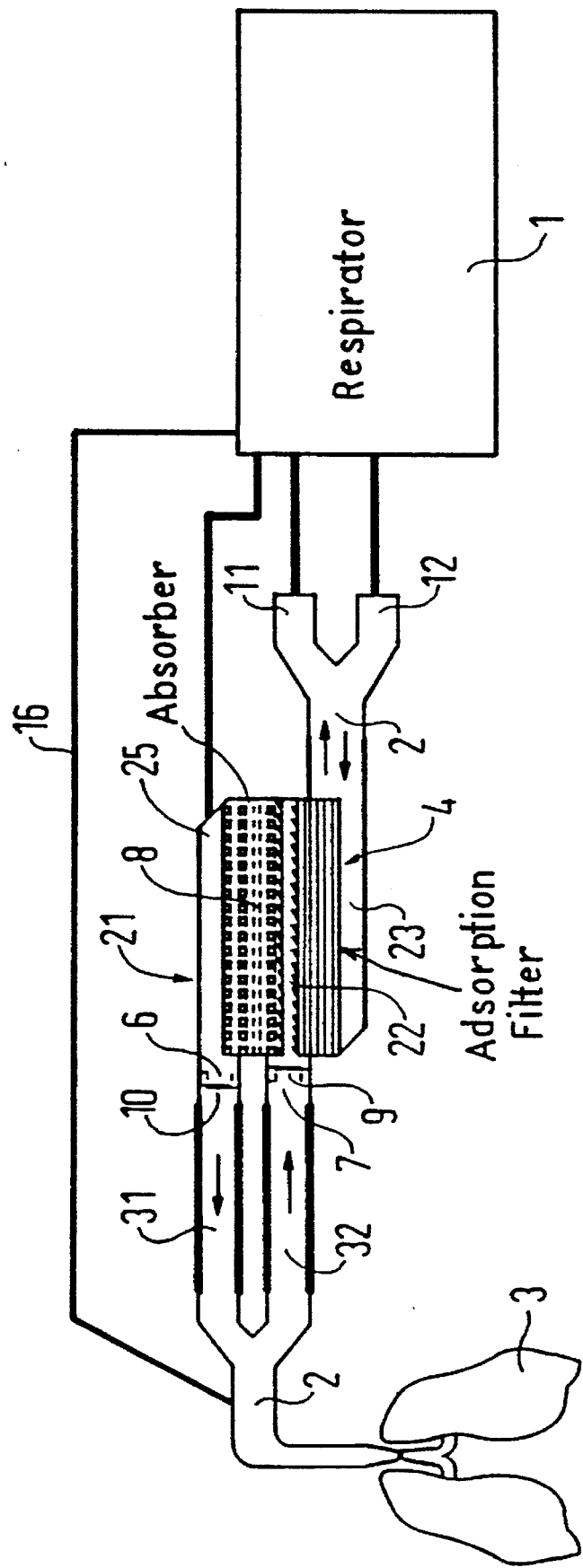

If, for whatever reason, the anesthesiologist does not wish to place the arrangement in the proximity of the patient, the inhalation and exhalation branches 6 and 7 can be lengthened with patient hoses 31 and 32, as shown in FIG. 3. These are connected to the common line 2. The arrangement is just as effective as if it were directly connected to the patient 3, with the "dead space" being maintained just as low as in the embodiment of FIG. 2.

It has been shown that carbon, particularly coconut shell charcoal or wood charcoal, is extremely well-suited for the adsorption filter 4. The carbon also adsorbs a a large amount of moisture from the exhalation gas, which is desorbed in the inhalation phase and is mixed with the remaining inhalation gas. A very good moisture-heat exchanger is thereby established.

The container 21 in the embodiments of FIGS. 2 and 3 which contains the adsorption material 5 and the absorber 8 is inexpensive to manufacture due to its small size and simplicity, and is therefore suitable as a disposable product. After one treatment, the container 21 is separated from the patient hoses, and from the other lines, and is replaced by a new container.

Although modifications and changes may be suggested by those skilled in the art, it is the intention of the inventors to embody within the patent warranted hereon all changes and modifications as reasonably and properly come within the scope of their contribution to the art.

We claim as our Invention:

1. A method for re-using anesthetic gases in inhalation anesthesia comprising the steps of:

ventilating a patient with an anesthetic gas and respiration gas, the patient, in an exhalation phase having an exhalation resistance associated therewith, thereby producing exhaled gas containing anesthetic gas which was not absorbed by said patient and carbon dioxide, and a remainder of exhaled gas;

directing the exhaled gas through an adsorption filter for adsorbing said anesthetic gas which was not absorbed by the patient during respiration and thereby simultaneously unavoidably adsorbing a small amount of said carbon dioxide;

passing said remainder of exhaled gas through said adsorption filter and evacuating said remainder of exhaled gas;

in a subsequent inhalation phase, directing fresh respiration gas through said adsorption filter so that the anesthetic gas and said small amount of carbon dioxide previously adsorbed by said adsorption filter are desorbed into said fresh respiration gas;

minimizing said exhalation resistance by matching a carbon dioxide absorption capacity of a carbon dioxide absorber to said small amount of carbon dioxide so that said carbon dioxide absorber absorbs no more than said small amount of carbon dioxide any by positioning said carbon dioxide absorber in an inhalation line, separate from said exhalation line, between said adsorption filter and said patient;

directing the fresh respiration gas which has passed through the adsorption filter through said inhalation line so that said carbon dioxide absorber absorbs said small amount of carbon dioxide without significant breathing resistance to said patient;

additionally directing at least one of fresh respiration gas and fresh anesthetic gas through a line bypassing said adsorption filter and said carbon dioxide absorber;

combining the additionally directed fresh gas with the fresh respiration gas which has passed through said adsorption filter and said carbon dioxide absorber in a desired gas concentration to form a mixture and supplying said mixture to said patient.

2. A method as claimed in claim 1 comprising the additional steps of:

measuring the gas concentration of said mixture supplied to said patient; and controlling the supply of additionally directed fresh gas to maintain said desired gas concentration of said mixture.

3. A method as claimed in claim 2 wherein the step of controlling the supply of said additionally directed fresh gas is further defined by the step of controlling the supply of additionally directed fresh gas by feedback by forming an actual value from the measured gas concentration and using said desired gas concentration as a rated value.

4. A method as claimed in claim 1 comprising the additional step of:

using carbon as adsorption material in said adsorption filter.

5. An apparatus for re-using anesthetic gases in inhalation anesthesia comprising:

means adapted for connection to a patient via a connector for ventilating the patient with an anesthetic gas and respiration gas, the patient thereby producing exhaled gas, in an exhalation line, containing anesthetic gas which was not absorbed by said patient and carbon dioxide, and a remainder of exhaled gas;

adsorption filter means communicating with said exhalation line for adsorbing said anesthetic gas in said exhaled gas which was not absorbed by the patient during respiration, and thereby simultaneously unavoidably adsorbing a small amount of said carbon dioxide in said exhaled gas, and for permitting said remainder of exhaled gas to pass through said adsorption filter means;

means for evacuating said remainder of exhaled gas;

said means for ventilating, in a subsequent inhalation phase, directing fresh respiration gas through said adsorption filter means so that the anesthetic gas and said small amount of carbon dioxide previously adsorbed by said adsorption filter means are desorbed into said fresh respiration gas;

a carbon dioxide absorber disposed in an inhalation line, separate from said exhalation line, between said adsorption filter and said connector;

means for directing said fresh respiration gas which has passed through said adsorption filter means through said carbon dioxide absorber for absorbing said small amount of carbon dioxide;

a bypass line bypassing said adsorption filter means and said carbon dioxide absorber;

means for directing at least one of fresh respiration and fresh anesthetic gas from said means for ventilating through said bypass line;

means for combining the gas directed through said bypass line with the fresh gas which has passed through said adsorption filter means and said carbon dioxide absorber in a desired gas concentration for forming a mixture and for supplying said mixture to said connector; and an inhalation branch and an exhalation branch communicating with said connector and a main conduit connected to an input of said means for ventilating, said adsorption filter means and said carbon dioxide absorber being disposed in parallel in a single container, said container having a first channel between said adsorption filter means and said carbon dioxide absorber, a second channel formed between said adsorption filter and a first inside wall of said container, and a third channel formed between said carbon dioxide absorber and a second inside wall of said container, said first channel being connected to said exhalation branch, said second channel being connected to said main conduit at a side of said adsorption filter means facing away from said connector, and said third channel being connected to said inhalation branch.

6. An apparatus for re-using anesthetic gases in inhalation anesthesia comprising:

means adopted for connection to a patient via a connector for ventilating the patient with an anesthetic gas and respiration gas, the patient thereby producing exhaled gas, in an exhalation line, containing anesthetic gas which was not absorbed by the patient and carbon dioxide, and a remainder of exhaled gas;

an adsorption filter means communicating with said exhalation line for directing the exhaled gas through said adsorption filter means for adsorbing said anesthetic gas in said exhaled gas which was not absorbed during respiration, and thereby simultaneously unavoidably adsorbing a small amount of said carbon dioxide and for permitting said remainder of exhaled gas to pass through said adsorption filter means;

means for evacuating said remainder of exhaled gas;

said means for ventilating, in a subsequent inhalation phase, directing fresh respiration gas through said adsorption filter means so that the anesthetic gas and said small amount of carbon dioxide previously adsorbed by said adsorption filter means are desorbed into said fresh respiration gas;

an inhalation line, separate from said exhalation line;

carbon dioxide absorber means, disposed in said inhalation line between said adsorption filter means and said connector, for minimizing said exhalation resistance by its placement in said inhalation line and by having a carbon dioxide absorption capacity matched to said small amount of carbon dioxide for adsorbing no more than said small amount of carbon dioxide;

means for directing said fresh respiration gas which has passed through said adsorption filter means through said carbon dioxide absorber for absorbing said small amount of carbon dioxide;

a bypass line bypassing said adsorption filter and said carbon dioxide absorber;

means for directing at least one of fresh respiration and fresh anesthetic gas from said means for ventilating through said bypass line; and means for combining the gas directed through said bypass line with the fresh gas which has passed through said adsorption filter means and said carbon dioxide absorber in a desired gas concentration for forming a mixture and for supplying said mixture to said connector.

7. An apparatus as claimed in claim 6 wherein said adsorption material is carbon.

8. An apparatus as claimed in claim 7 wherein said carbon is coconut shell charcoal.

9. An apparatus as claimed in claim 7 wherein said carbon is wood charcoal.

10. An apparatus as claimed in claim 6 further comprising:

a germ filter following said adsorption filter means disposed at a side of said adsorption filter means facing away from the connector.

11. An apparatus as claimed in claim 6 further comprising:

a main conduit connected to an input of said means for ventilating;

a measurement conduit connected to said main conduit at a location between said patient and said carbon dioxide absorber;

means for measuring a gas concentration of at least one type of gas connected to said measurement conduit for measuring a gas concentration of said mixture supplied to said patient, and for generating a control signal corresponding to the measured gas concentration of said mixture; and feedback-controlled means connected to said means for measuring a gas concentration for controlling the delivery of at least one of said fresh anesthetic gas and said fresh respiration gas to said patient via said means for combining, dependent on said control signal for forming a desired gas concentration of said mixture.

* * * * *